United States Patent
Hartlep et al.

(10) Patent No.: US 7,471,974 B2
(45) Date of Patent: Dec. 30, 2008

(54) METHOD FOR PLANNING STIMULATION OF HYPER/HYPOMETABOLIC CORTICAL AREAS

(75) Inventors: Andreas Hartlep, München (DE); Philipp Tanner, München (DE); Peter Eichhammer, Burglengenfeld (DE); Berthold Langguth, Regensburg (DE)

(73) Assignee: BrainLAB AG, Feldkirchen (DE)

( * ) Notice: Subject to any disclaimer, the term of this patent is extended or adjusted under 35 U.S.C. 154(b) by 147 days.

(21) Appl. No.: 10/661,463

(22) Filed: Sep. 12, 2003

(65) Prior Publication Data

US 2004/0138550 A1 Jul. 15, 2004

Related U.S. Application Data

(60) Provisional application No. 60/437,585, filed on Dec. 31, 2002.

(30) Foreign Application Priority Data

Sep. 13, 2002 (EP) .................... 02020517

(51) Int. Cl.
*A61B 5/05* (2006.01)
(52) U.S. Cl. ...................... 600/424; 600/407
(58) Field of Classification Search ............ 600/11, 600/12, 13, 407–480, 544, 554, 373, 378, 600/4; 607/55, 56, 115, 116
See application file for complete search history.

(56) References Cited

U.S. PATENT DOCUMENTS

| 5,644,234 | A | | 7/1997 | Rasche et al. | |
|---|---|---|---|---|---|
| 5,820,588 | A | * | 10/1998 | Howard, III | 604/93.01 |
| 6,129,685 | A | * | 10/2000 | Howard, III | 600/585 |
| 6,196,226 | B1 | * | 3/2001 | Hochman et al. | 600/425 |
| 6,298,259 | B1 | * | 10/2001 | Kucharczyk et al. | 600/411 |
| 6,301,492 | B1 | * | 10/2001 | Zonenshayn | 600/378 |
| 6,425,852 | B1 | | 7/2002 | Epstein et al. | |
| 2002/0087062 | A1 | | 7/2002 | Dombay et al. | |

OTHER PUBLICATIONS

Ettinger, G.J. et al. "Non-Invasive Functional Brain Mapping using Registered Transcranial Magnetic Stimulation." *Proceedings of the IEEE Workshop on Mathematical Methods in Biomedical Image Analysis*. (Jun. 1996): 32-41.

Herwig, U. et al. "Neuronavigation in der Psychiatrie—fokussierte transkranielle Magnetstimulation bei depressiven Patienten." *Nervenheilkunde*. 7.18 (1999): 353-357.

(Continued)

*Primary Examiner*—Brian L. Casler
*Assistant Examiner*—Nasir Shahrestani
(74) *Attorney, Agent, or Firm*—Renner, Otto, Boiselle & Sklar, LLP

(57) ABSTRACT

A method for planning the stimulation of hyper/hypometabolic cortical areas includes determining anatomical patient data using an imaging method and detecting positions of (i) the hyper/hypometabolic cortical areas in a patient's anatomy and (ii) a position of a stimulator. The positions of the hyper/hypometabolic cortical areas are registered and/or referenced with respect to the position of the stimulation means. An optimal positioning for the stimulator is determined on the basis of the relative positional information.

11 Claims, 1 Drawing Sheet

OTHER PUBLICATIONS

Ettinger, G.J. et al. "Non-Invasive Functional Brain Mapping Using Registered Transcranial Magnetic Stimulation." *IEEE Proceedings of MMBIA*. (1996): 32-41.

Herwig, U. et al. "Neuronavigation in der Psychiatrie—fokussierte transkranielle Magnetstimulation bei depressiven Patienten." *Nervenheilkunde*. 7.18 (1999): 353-357.

* cited by examiner

METHOD FOR PLANNING STIMULATION OF HYPER/HYPOMETABOLIC CORTICAL AREAS

RELATED APPLICATION DATA

This application claims priority of U.S. Provisional Application No. 60/437,585, filed on Dec. 31, 2002, which is incorporated herein by reference in its entirety.

FIELD OF THE INVENTION

The present invention relates generally to planning the stimulation of hyper/hypometabolic cortical areas and, more particularly, to planning the magnetic stimulation, of hypermetabolic cortical areas, which are related to the manifestation of systemic tinnitus.

BACKGROUND OF THE INVENTION

Magnetically stimulating cortical areas is above all known from so-called "brain mapping", in which brain functions are directly and indirectly mapped, in order to enable particular functional areas of the brain to be located.

A method is known from U.S. Pat. No. 5,738,625 for magnetically stimulating nerve cells. U.S. Pat. No. 5,644,234 describes a nuclear spin resonance (MR) method in which the intention is to determine the position of a micro-coil in an object. A method and a device for transcranial magnetic stimulation of the brain are known from WO 98/06342, in which a roughly hemispherical magnetic core wound by coils is used to generate a stimulation signal. The device and method described are intended to localize the function of speech.

U.S. Pat. No. 6,394,969 describes tinnitus masking and a suppressing device for applying pulsed ultrasound. U.S. Pat. No. 6,366,813 describes a device and a method for intracranial stimulation to optimally examine neurological diseases. U.S. Pat. No. 6,402,678 describes a means and a method for treating migraines. U.S. Pat. No. 6,425,852 describes a device and a method for transcranial magnetic brain stimulation, to include treating depression and localizing and characterizing speech difficulties.

U.S. Pat. No. 6,258,032 describes a method for diagnosing and treating the symptoms of vasospasm. U.S. Pat. No. 6,132,361 describes transcranial brain stimulation. U.S. Pat. No. 5,769,778 describes magnetic, non-convulsive stimulation therapy. U.S. Pat. No. 5,061,234 describes a magnetic neural stimulator for neurophysiology. DE 39 37 793 A1 describes a device for inductively stimulating excitable tissue. DE 44 08 110 A1 describes a method and a device for neuromagnetic stimulation. DE 199 14 762 A1 describes an arrangement of coils for transcranial magnetic stimulation. DE 199 52 191 C1 describes a device for magnetically stimulating neurones and/or nerve fibers using a coil, and an application for means for cooling the coils.

SUMMARY OF THE INVENTION

One object of the present invention is to propose a method for planning the stimulation of hyper/hypometabolic cortical areas, in which it is ensured that the stimulation means is optimally positioned. In particular, it is an object of the present invention to provide a planning method such as is suitable for stimulating, for example, magnetically stimulating, hypermetabolic cortical areas which are related to the manifestation of systemic tinnitus.

According to one aspect of the invention, the invention is directed to a method for planning the stimulation of hyper/hypometabolic cortical areas. Anatomical patient data can be determined using an imaging method and the position of the hyper/hypometabolic cortical areas in the patient's anatomy as well as the position of a stimulation means can be detected using a medical navigation system. The position of the hyper/hypometabolic cortical areas can be registered and/or referenced with respect to the position of the stimulation means and the optimal positioning for the stimulation means can be planned on the basis of the relative positional information.

Optimal planning can be provided by incorporating the medical navigation system into planning the stimulation of the hyper/hypometabolic cortical areas, ensuring that the desired cortical areas are stimulated with a high hitting accuracy. For the first time, this enables stimulation to be planned for cortical areas such as are related to the manifestation of systemic tinnitus.

In one embodiment, the method includes, while determining the anatomical patient data, determining functional anatomical data using functional image detection methods, such as functional magnetic resonance detection and/or positron emission tomography (PET). In addition, structural anatomical data, which can be positionally assigned in the navigation system, can be determined using conventional image detection methods, such as magnetic resonance detection and/or nuclear spin tomography. The functional anatomical data can then be navigationally registered and/or referenced with the structural anatomical data using a computer-assisted matching method, such as a graphical matching method, such that the functional anatomical data are available for navigation. Using such an embodiment variant, such functional anatomical data and structural anatomical data can be assigned, and integrated within the framework of planning, in order to ensure optimal navigation and tracking for a successful treatment.

In one embodiment, the navigation system used in conjunction with the invention can be one based on optically detecting arrangements of actively or passively emitting markers arranged on the patient, such as on the patient's head, and on the stimulation means. Instead of or in addition to this, a navigation system can be used, which is based on magnetically and/or inductively detecting positional means, such as coils and/or oscillating circuits, arranged on the patient's head, and on the stimulation means. In one embodiment, the stimulation means can include a cortical stimulation coil. However, other stimulation means can be included.

In one embodiment, the detected navigational data can be outputted together with the planning results, on an image output.

In another embodiment, the stimulation means or coil is calibrated within the framework of planning. Furthermore, a computer-assisted field distribution can be simulated for the stimulation means or coil within the framework of planning, with the aid of which the stimulation areas are determined.

The invention further relates to a program, which, when it is run on a computer or is loaded onto a computer, causes the computer to perform a method such as described above. In addition, the invention relates to a computer program storage medium comprising such a program.

BRIEF DESCRIPTION OF THE DRAWINGS

These and further features of the present invention will be apparent with reference to the following description and drawings, wherein.

DETAILED DESCRIPTION OF THE INVENTION

Figure 1:
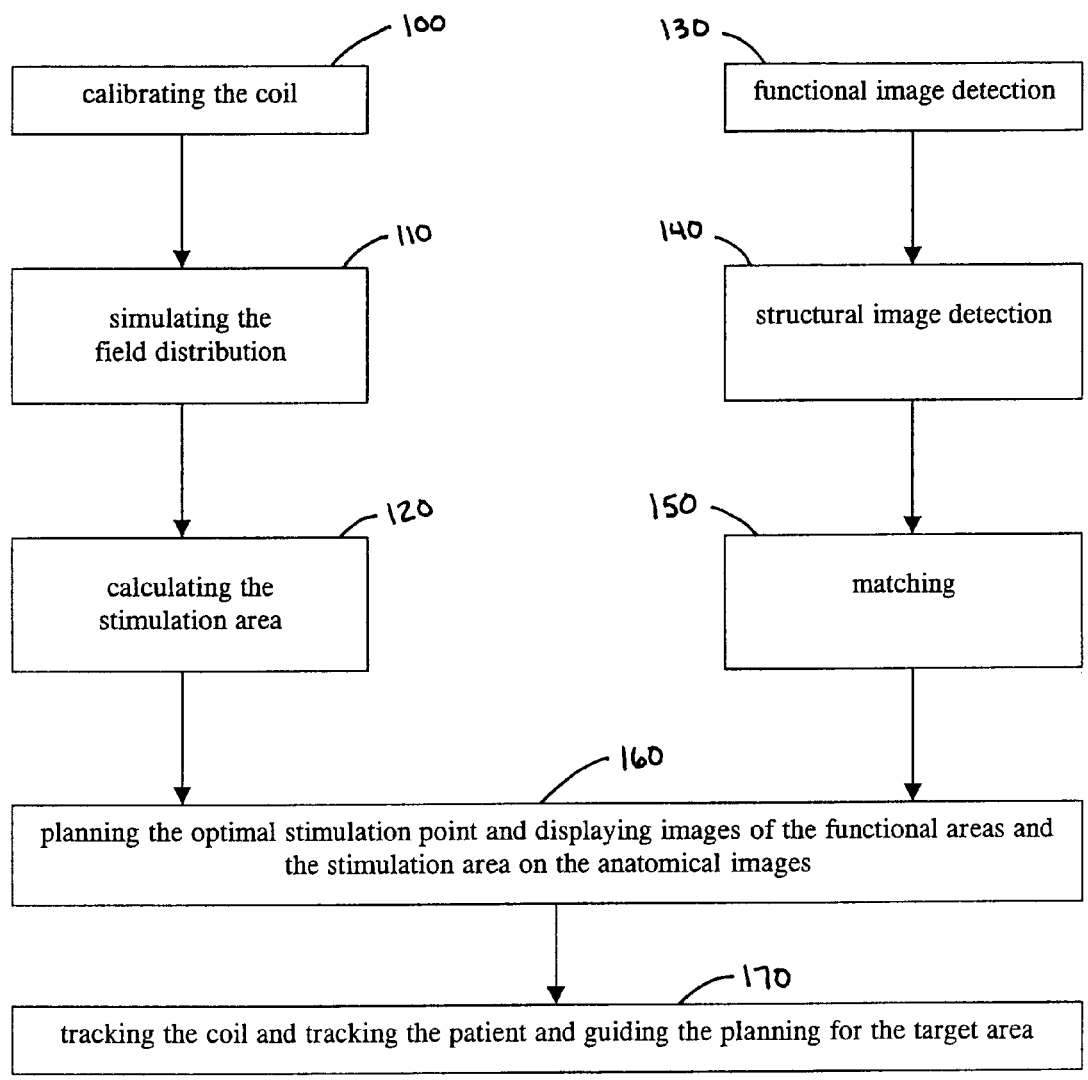
FIG. 1 is a flow chart illustrating a method for planning stimulation of hyper/hypometabolic cortical areas in accordance with the invention.

With reference to FIG. 1, a method of planning for treating tinnitus using navigated, transcranial magnetic stimulation is provided. In the first phase, two parts of the process can proceed independently of each other and possibly in parallel. In a first part of the process, a stimulation coil is prepared, using which a magnetic field is generated which will stimulate the hyper/hypometabolic cortical areas during the treatment. To this end, the coil can be calibrated 100 and then the field distribution is simulated 110 (e.g., computer simulation). This field distribution can be very elaborately simulated 110, consistent with the way it will actually be in the area of the brain structure. It is to be appreciated that the magnetic field here is designed very much more complicated than in the field design without an "interfering" brain structure.

Once it is then known what the field distribution looks like, it can also be calculated 120 where the stimulation area proceeding from the coil will be relative to the position of the coil. In order to positionally track the coil, it is provided with navigation markings (optical, magnetic) and can, therefore, be tracked in a navigation system. Such navigation systems include those described in co-owned U.S. Pat. No. 6,351,659, which is incorporated herein by reference in its entirety. In this way, the previously simulated and/or calculated stimulation areas can also be tracked, whose positional relationship to the coil has been determined in advance as outlined above.

With continued reference to FIG. 1, separate from, and, optionally, in parallel with, the above process sequence 100, 110, 120, image detection can be performed on a tinnitus patient. In one embodiment, this image detection includes functional image detection 130, in which functional magnetic resonance detection or positron emission tomography and/or other suitable methods can be used to establish where the functional cortical areas, to be stimulated, are situated in the patient. In the present case, in which the primary and secondary auditory cortex are to be located, the patient can be, for example, exposed to sound stimuli, and, using functional image detection, it can be determined which area of the cortex responds. These functional images can be used to determine the area of hypermetabolic activities in the brain, which is related to the manifestation of systemic tinnitus.

Furthermore, and independently of the functional image detection 130, structural images of the patient are produced 140, for example, using nuclear spin tomography, CT or other suitable methods. Detecting these structural images 140 can be incorporated into a navigation system in a known way by using markers on the head of the patient, in such a way that the positions of the brain structure are available with respect to the markers, and, therefore, in the navigation system. In the next step, namely that of matching 150s, the structural images 140 generated are registered with respect to the functional images 130 in order to provide the spatial position of particular functional cortical areas. A graphical, computer-assisted matching method can be used here, which assigns the data of the anatomical areas determined, for example, by way of structural boundaries recognizable in the images.

After matching 150, an anatomical patient data set is accordingly obtained from this part of the process sequence, with or on which navigation is possible and which shows the functional areas. This image data set can then be used to navigate the prepared coil, thus enabling the optimal stimulation point to be planned and an image of the functional areas and the stimulation area to be shown on the anatomical images 160. In one embodiment employing a combined stimulation-neuronavigation system, the areas to be stimulated can be shown on an image display, for example, a screen, in order to treat the tinnitus. In addition, the navigation system is capable of detecting the spatial position of the coil and the head 170 and detecting and displaying the actual and planned position of maximum stimulation, in order to guide a physician carrying out the treatment to the correct stimulation area (the target area).

Although particular embodiments of the invention have been described in detail, it is understood that the invention is not limited correspondingly in scope, but includes all changes, modifications and equivalents.

What is claimed is:

1. A method for planning stimulation of hyper/hypometabolic cortical areas, the method comprising:
   simulating a field distribution for a stimulator relative to a position of the stimulator;
   determining a stimulation area for the stimulator relative to a position of the stimulator;
   determining functional anatomical patient data;
   determining structural anatomical patient data;
   navigationally registering the functional anatomical data with the structural anatomical data such that the functional anatomical data are available for navigation;
   based on the functional anatomical data, detecting positions of the hyper/hypometabolic cortical areas in a patient's anatomy;
   determining a position of a stimulator;
   navigationally registering the stimulation area of the stimulator;
   at least one of (i) registering or (ii) referencing the position of the hyper/hypometabolic cortical areas with respect to the position of the stimulator;
   determining an optimal positioning for the stimulator on the basis of relative positional information of the hyper/hypometabolic cortical areas and the stimulation area of the stimulator; and
   displaying the optimal positioning for the stimulator.

2. The method as set forth in claim 1, wherein the detecting step is performed using a medical navigation system.

3. The method as set forth in claim 1, wherein the stimulation is planned of hypermetabolic areas related to the manifestation of systemic tinnitus.

4. The method as set forth in claim 1, wherein the functional image detection method includes at least one of (i) functional magnetic resonance detection and (ii) positron emission tomography (PET).

5. The method as set forth in claim 1, wherein the detecting step includes using a navigation system to optically detect arrangements of actively or passively emitting markers arranged on the patient's head and on the stimulation means.

6. The method as set forth in claim 1, wherein the detecting step includes using a navigation system to magnetically or inductively detect (i) at least one of (a) positional coils and (b) oscillating circuits, arranged on the patient's head and on the stimulator.

7. The method as set forth in claim 1, wherein the stimulator includes a cortical stimulation coil.

8. The method as set forth in claim 2, further comprising:
   outputting detected navigational data together with the determined optimal positioning on an image output.

9. The method as set forth in claim 1, further comprising:
   calibrating the stimulator.

10. A computer program storage medium comprising a program which, when it is run on a computer or is loaded onto a computer, causes the computer to perform a method in accordance with claim 1.

11. A method of stimulating hyper/hypometabolic cortical areas of a patient, the method comprising:
- simulating a field distribution for a stimulation coil relative to a position of the stimulation coil;
- determining a stimulation area for the stimulation coil relative to a position of the coil;
- determining functional anatomical patient data;
- determining structural anatomical patient data;
- navigationally registering the functional anatomical data with the structural anatomical data such that the functional anatomical data are available for navigation;
- based on the functional anatomical data, detecting positions of the hyper/hypometabolic cortical areas in a patient's anatomy;
- detecting the position of the stimulation coil;
- navigationally registering the stimulation area of the stimulation coil;
- registering the position of the functional anatomical data with respect to the position of the stimulation coil;
- positioning the stimulation coil on the basis of the relative positional information of the hyper/hypometabolic cortical areas and the stimulation area of the stimulation coil; and;
- stimulating the hyper/hypometabolic cortical areas of the patient.

* * * * *